United States Patent

Kujath et al.

Patent Number: 5,179,206
Date of Patent: Jan. 12, 1993

[54] SUBSTITUTED 3-AMINOSYDNONE IMINES

[75] Inventors: Eckard Kujath, Maintal; Christian Baumgartner, Stuttgart; Karl Schönafinger, Alzenau; Rudi Beyerle, Frankfurt; Melitta Just, Nidderau; Helmut Bohn, Schöneck; Jörg Ostrowski, Rodenbach, all of Fed. Rep. of Germany

[73] Assignee: Cassella Aktiengellschaft, Fed. Rep. of Germany

[21] Appl. No.: 534,832

[22] Filed: Jun. 7, 1990

[30] Foreign Application Priority Data

Jul. 3, 1989 [DE] Fed. Rep. of Germany ....... 3921796

[51] Int. Cl.$^5$ ............................................. C07D 413/04
[52] U.S. Cl. ................................................ 546/209
[58] Field of Search ......................... 548/125; 546/209

[56] References Cited

U.S. PATENT DOCUMENTS 4,937,244 6/1990 Schönafinger ..................... 514/252

FOREIGN PATENT DOCUMENTS 1198283 7/1970 United Kingdom ............... 548/125

Primary Examiner—Robert Gerstl
Attorney, Agent, or Firm—Perman & Green

[57] ABSTRACT

Substituted 3-aminosydnone imines of the formula I

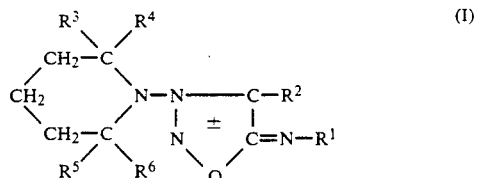

and their pharmacologically acceptable acid addition salts, in which $R^1$ denotes e.g. hydrogen;
$R^2$ denotes e.g. an alkyl radical;

at least two of the radicals $R^3$, $R^4$, $R^5$ and $R^6$ denote alkyl radicals and the others denote hydrogen, are prepared by cyclization of a compound of the formula II

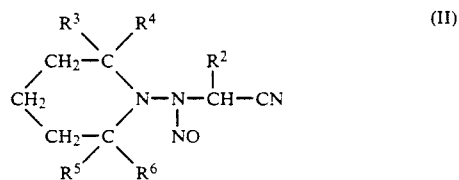

and, if appropriate, subsequent acylation, and have useful pharmacological properties.

9 Claims, No Drawings

SUBSTITUTED 3-AMINOSYDNONE IMINES

BACKGROUND OF THE INVENTION

The present invention relates to novel N-piperidino sydnone imines, and to novel N-piperidino amino acetonitriles for producing such sydnone imines, and to processes for the preparation of such compounds. The invention also relates to pharmaceutical compositions containing the present sydnone imine or acetronitrile compounds, and to the preparation and use of such compositions for the control or prophylaxis of disorders of the cardiovascular system, including angina pectoris, functioning as antihypertensive medicaments, for example.

DESCRIPTION OF THE ART

The novel compounds and compositions of the present invention have been found to have considerably prolonged duration of action and potency as compared to known 3-amino sydnone imines such as molsidomine.

SUMMARY OF THE INVENTION

The invention relates to pharmacologically active substituted 3-aminosydnone imines of the general formula I

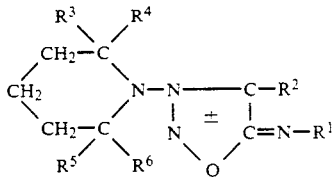

and their pharmacologically acceptable acid addition salts, in which $R^1$ denotes hydrogen or the radical —$COR^7$;

$R^2$ denotes an alkyl radical having 1 to 8 C atoms or an optionally substituted aralkyl radical having 1 to 4 C atoms in the alkyl radical and 6 to 12 aryl C atoms;

$R^3$, $R^4$, $R^5$ and $R^6$ denote hydrogen or an alkyl radical having 1 to 4 C atoms;

$R^7$ denotes an aliphatic radial having 1 to 4 C atoms, which may also be substituted by alkoxy having 1 to 4 C atoms; a cycloaliphatic radical having 5 to 7 C atoms; a bicycloaliphatic radical having 7 to 14 C atoms; a tricycloaliphatic radical having 7 to 16 C atoms; an alkoxy radical having 1 to 6 C atoms; an aryloxy radical having 6 to 10 C atoms; an alkoxycarbonyl radical having a total of 2 to 7 C atoms; an aryl radical having 6 to 10 C atoms; an aryl radical having 6 to 10 C atoms, which is mono-, di- or trisubstituted by 1 to 3 halogen atoms and/or 1 to 3 alkyl radicals having 1 to 3 C atoms and/or 1 to 3 alkoxy radicals having 1 to 3 C atoms and/or 1 or 2 nitro groups, where at least two of the radicals $R^3$, $R^4$, $R^5$ and $R^6$ are alkyl radicals.

The invention further relates to a process for the preparation of the compounds of the formula I according to the invention, to the N-substituted N-nitroso-amino-acetonitriles of the general formula II

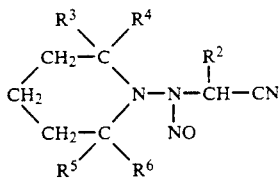

used for the preparation of the compounds of the formula I, in which $R^2$, $R^3$, $R^4$, $R^5$ and $R^6$ have the meanings already mentioned and at least two of the radicals $R^3$, $R^4$, $R^5$ and $R^6$ are alkyl radicals, and to their use.

Aliphatic radicals, alkyl radicals and alkoxy radicals may be straight-chain or branched. This also applies if they occur as substituents of other radicals, e.g. as substituents of aryl radicals, or in combination with other radicals, e.g. as aralkyl or as alkoxycarbonyl.

The aralkyl radicals representing $R^2$ may be unsubstituted in the aryl radical or mono-, di- or trisubstituted by 1 to 3 halogen atoms and/or 1 to 3 alkyl radicals having 1 to 4 C atoms and/or 1 to 3 alkoxy radicals having 1 to 4 C atoms and/or 1 to 2 nitro groups and/or 1 to 2 hydroxyl groups and/or 1 to 3 alkylthio radicals having 1 to 4 C atoms and/or a trifluoromethyl radical.

Aryl radicals having 6 to 10 C atoms, which may also be optionally substituted, are e.g. phenyl and α- or β-naphthyl. Aryl radicals having 6 to 12 C atoms, which occur in connection with an aralkyl radical representing $R^2$ and which may also be substituted, are e.g.: phenyl, α- or β-naphthyl or biphenylyl.

$R^2$ preferably denotes an alkyl radical having 1 to 8 C atoms, in particular having 1 to 6 C atoms, or a phenylalkyl radical having 1 to 4 C atoms, in particular 1 or 2 C atoms, in the alkyl radical.

Alkyl radicals representing $R^3$, $R^4$, $R^5$ and $R^6$ may be identical or different. As a rule, they are identical. Suitable radicals for $R^3$ to $R^6$ are above all straight-chain alkyl radicals; methyl radicals are preferred.

Preferably, two of the radicals $R^3$, $R^4$, $R^5$ and $R^6$ are alkyl radicals, preferably methyl radicals, it being possible for these two alkyl radicals to be bonded both to the same C atom of the piperidine ring (C-2 or C-6) and to different C atoms of the piperidine ring (C-2 and C-6). Particularly preferably, one of these two alkyl radicals, in particular methyl radicals, is bonded to C-2, and the other to C-6. These two alkyl radicals can be both in a cis-position and in a trans-position. C-2 and C-6 of the piperidine ring may have, optionally independently of one another, both the R-configuration and the S-configuration. The invention includes both the possible individual stereoisomers of the general formula I and mixtures of several stereoisomers of the general formula I having any composition.

Suitable aliphatic radicals representing $R^7$ are in particular alkyl radicals having 1 to 4 C atoms. As aliphatic radicals representing $R^7$, which are substituted by alkoxy having 1 to 4 C atoms, the methoxymethyl radical is to be mentioned in particular. Suitable cycloaliphatic radicals representing $R^7$ are above all cycloalkyl radicals having 5 to 7 C atoms, in particular cyclopentyl, and preferably cyclohexyl. A suitable bicycloaliphatic radical representing $R^7$ is in particular 2,6,6-trimethyl-bicyclo(3.1.1)heptan-3-yl (=3-pinanyl).

A suitable tricycloaliphatic radical representing $R^7$ is in particular tricyclo(3.3.1.1$^{3,7}$)decan-1-yl (=adamantanyl). Suitable alkoxy radicals representing $R^7$ are in particular methoxy and ethoxy radicals. A suitable alkoxy carbonyl radical representing $R^7$ is in particular the ethoxycarbonyl radical. As aryl radicals representing $R^7$, e.g. α- or β-naphthyl radicals, but in particular the phenyl radical, may be mentioned. As aryloxy radicals representing $R^7$, e.g. α- or β-naphthoxy radicals, but in particular the phenoxy radical, may be mentioned. The aryl radicals representing $R^7$ can be mono-, or di- or trisubstituted, where, however, even on trisubstitution only a maximum of 2 nitro groups can be present, such as, for example, 2-methyl-4,6-dinitrophenyl and 2-chloro-6-methyl-4-nitrophenyl. Suitable halogen substituents for the aryl radicals are e.g. chlorine and bromine atoms. Substituted aryl radicals representing $R^7$ which may be mentioned in particular are: methylphenyl (=tolyl), nitrophenyl, chlorophenyl and methoxyphenyl.

$R^1$ preferably denotes hydrogen, ethoxycarbonyl or benzoyl. Preferred compounds of the formula I are those which contain one or, in particular, more of the preferred, above all the particularly preferred, radicals.

The pharmacologically acceptable acid addition salts are particularly preferred, in particular the hydrochlorides of 4-benzyl-3-(2,6-dimethylpiperidino)-sydnone imine and 3-(2,6-dimathylpiperidino)-4-(2-phenethyl)-sydnone imine.

A compound of the general formula I can be prepared by a process in which a compound of the general formula II is cyclized to a compound of the general formula Ia

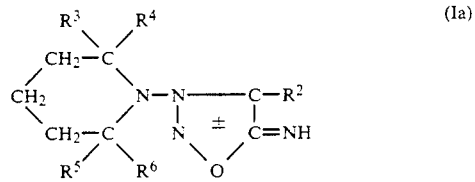

and in which this or an acid addition salt thereof, in the case in which a compound of the formula I with $R^1=-COR^7$ is intended to be prepared, is acylated with an acylating agent which introduces the radical $-COR^7$, and the compound thus obtained is optionally converted into a pharmacologically acceptable acid addition salt.

The cyclization of the compounds II to the compounds Ia is carried out in a suitable organic or inorganic solvent or dispersant with the addition of a cyclizing agent, normally at temperatures from 0° to 40° C., preferably at 0° to 20° C. Suitable cyclizing agents are those which give a pH below 3 in aqueous solution, that is e.g. mineral acids, such as sulphuric, nitric or phosphoric acid, preferably hydrogen chloride, but also strong organic acids, such as trifluoroacetic acid. The corresponding acid addition salt of the compound Ia is normally obtained in the cyclization.

Suitable solvents or dispersants are e.g.: alcohols, in particular those having 1 to 6 C atoms, preferably those having 1 to 4 C atoms, such as e.g. methanol, ethanol, i- and n-propanol, i-, sec- and tert-butanol, n-, i-, sec- and tert-pentanol, n-hexanol, cyclopentanol, cyclohexanol; ethers, in particular those having 2 to 8 C atoms in the molecule, such as e.g. diethyl ether, methyl ethyl ether, di-n-propyl ether, di-isopropyl ether, methyl n-butyl ether, ethyl propyl ether, di-butyl ether, tetrahydrofuran; 1,4-dioxane, 1,2-dimethoxyethane, bis-β-methoxyethyl ether; oligoethylene glycol dimethyl ethers, such as e.g. pentaglyme; carboxylic acid alkyl esters, in particular those having 3 to 8 C atoms in the molecule, such as e.g. methyl acetate or ethyl acetate; ketones, in particular those having 3 to 10 C atoms in the molecule, such as e.g. acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, benzophenone, acetophenone; aliphatic hydrocarbons, such as e.g. hexane, heptane, low- and high-boiling petroleum ethers; cycloaliphatic hydrocarbons, such as e.g. cyclohexane, methylcyclohexane, tetralin, decalin; aromatic hydrocarbons, such as e.g. benzene, toluene, o-, m- and p-xylene, ethylbenzene; halogenated aliphatic or aromatic hydrocarbons, such as e.g. methylene chloride, chloroform, carbon tetrachloride, chlorobenzene, dichlorobenzene; hexamethylphosphoramide; sulphoxides, such as e.g. dimethyl sulphoxide; water. Mixtures of various solvents or dispersants can also be used, for example water methanol or preferably ethyl acetate methanol.

The compounds of the formula Ia represent compounds of the general formula I according to the invention in the case in which $R^1$ is hydrogen.

The acylation of the compound of the formula Ia, which may also be present in the form of an acid addition salt, to introduce the radical $R^1=-COR^7$ can be carried out in a manner known per se using a suitable acylating agent of the formula III

in which X represents a radical which can be eliminated by a nucleophile.

In the formula III, X denotes e.g., in particular, halogen, preferably —Cl or —Br; —OH; —O—alkyl, in particular having 1 to 5 C atoms; —O—aryl, where the aryl radical is in particular a phenyl radical, which may also be mono- or polysubstituted by alkyl, in particular methyl, and/or nitro, and, for example, is a tolyl, dinitrophenyl or nitrophenyl radical; —O—CO—$R^7$; —O—CO—O—alkyl, in particular having 1 to 5 C atoms in the alkyl radical, or the radical of an azole or benzazole having at least 2 N atoms in the quasi-aromatic 5-membered ring, which radical is bonded via an N atom.

The acylation is carried out in a suitable solvent or dispersant or in an excess of the acylating agent, expediently with stirring, at temperatures from 0° C. up to the boiling point of the solvent or acylating agent, in particular 0° to 50° C., preferably from 0° to 20° C.

The acylating agent of the formula III is expediently employed in the acylation of the compound of the formula Ia in an equivalent amount or in a small molar excess. Excesses of up to 30 mol % are as a rule sufficient, i.e. the molar ratio between the compound of the formula Ia and the acylating agent of the formula III is normally 1:(1 to 1.3), preferably 1:(1 to 1.2).

If an acid is eliminated in the acylation reaction, the addition of an acid scavenger, such as e.g. an alkali metal hydroxide, such as e.g. sodium hydroxide, potassium hydroxide or lithium hydroxide, a tertiary organic amine, such as e.g. pyridine or triethylamine, an alkali metal carbonate or alkali metal bicarbonate, such as e.g. sodium carbonate or sodium bicarbonate, or an alkali metal salt of a weak organic acid, such as e.g. sodium acetate, is expedient. Suitable catalysts, such as e.g. 4-dimethylaminopyridine, may also be added during the acylation reaction.

The compounds of the formula III are acylating agents and thus represent e.g.: for X=halogen: acid halides or haloformic acid esters, of which acid chlorides and chloroformic acid esters are preferred; for —OH: carboxylic acids; for —O—alkyl and —O—aryl: esters, of which the tolyl, 2,4-dinitro or 4-nitrophenyl esters are preferred; for —O—CO—$R^7$: anhydrides; for —O—CO—O—alkyl: mixed carboxylic acid/carbonic acid anhydrides; or heterocyclic amides or azolides. The acylating agents of the formula III can be prepared by processes known per se.

When using a carboxylic acid as the acylating agent, the addition of an activating agent, which has the object of increasing or activating the acylating potential of the carboxylic acid, or of converting the carboxylic acid into a reactive carboxylic acid derivative of the formula III in situ or preferably shortly before the reaction with the compound of the formula Ia, is expedient. Suitable activating agents of this type are e.g.: N,N'-disubstituted carbodiimides, in particular if they contain at least one secondary or tertiary alkyl radical, such as e.g. diisopropyl-, dicyclohexyl- or N-methyl-N'-tert.butyl-carbodiimide (compare Methodicum Chimicum, Verlag G. Thieme, Stuttgart, Vol. 6, (1974), p. 682/683, and Houben-Weyl, Methoden der Org. Chemie (Methods of Organic Chemistry), Vol. 8, (1952), p. 521/522); carbonic acid derivatives, such as e.g. phosgene, chloroformic acid esters, in particular having 1 to 5 C atoms in the alkyl radical (compare e.g. Tetrahedron Letters 24 (1983), 3365 to 3368); carbonic acid esters, such as e.g. N,N'-disuccinimidyl carbonate, diphthalimidyl carbonate, 1,1'-(carbonyldioxy)-dibenzo-triazole or di-2-pyridyl carbonate (compare e.g. Tetrahedron Letters, Vol. 25, No. 43, 4943-4946), if appropriate in the presence of suitable catalysts, such as e.g. 4-dimethylaminopyridine, N,N'-carbonyldiazoles, such as e.g. N,N'-carbonyl-diimidazole, 2,2'-carbonyl-1,2,3-ditriazole, 1,1'-carbonyl-1,2,4-ditriazole, N,N'-carbonyl-dipyrazole, 2,2'-carbonyl-ditetrazole, N,N'-carbonyl-benzimidazole or N,N'-carbonylbenzotriazole are further suitable as activating agents (compare e.g. H. A. Staab, M. Lü cking and F. H. Dürr, Chem. Ber. 95, (1962), 1275 et seq. H. A. Staab and A. Mannschreck, Chem. Ber. 95, (1962), 1284 et seq; H. A. Staab and W. Rohr, "Syntheses with Heterocyclic Amides (Azolides)" in "Neuere Methoden der Präparativen Organischen Chemie" (Newer Methods of Preparative Organic Chemistry), Volume V, Verlag Chemie, 1967, p. 53 et seq, in particular p. 65 to 69). The commercially available N,N'-carbonyldiimidazole is frequently used as the N,N'-carbonyldiazole. However, the other N,N'-carbonylazoles are also easily accessible from the respective azole and phosgene.

Further suitable activating agents for the carboxylic acid are: derivatives of oxalic acid, such as e.g. oxalyl chloride (compare e.g. GB-PS 2,139,225) or N,N'-oxalyl-diazoles such as e.g. 1,1'-oxalyldi-imidazole, 1,1'-oxalyldi-1,2,4-triazole and 1,1'-oxalyldi-1,2,3,4-tetrazole (compare e.g. Shizuaka Murata, Bull. Chem. Soc. Jap. 57, 3597-3598 (1984)); methylethylphosphinic anhydride (compare e.g. DE-OS 3,101,427); diphosphorus tetraiodide (Chem. Lett. 1983, 449); dialkyl disulphite (Indian J. Chem. 21, 259 (1982)); or other reactive agents.

The acylation of the compound of the formula Ia with the acylating agent III is carried out, as already mentioned, in a suitable solvent or dispersant or in an excess of the acylating agent. Suitable solvents or dispersants are e.g. those which have been given for carrying out the cyclization, moreover also e.g. pyridine and amides, such as e.g. dimethylformamide. In addition to water, polar organic solvents, such as dimethylformamide, dimethyl sulphoxide or pyridine are preferred for the acylation. Solvent mixtures, such as e.g. a mixture of water and methylene chloride, are also suitable.

The substituted 3-aminosydnone imines of the general formula I can form acid addition salts with inorganic or organic acids. Pharmacologically acceptable acid addition salts are. preferred. Inorganic or organic acids are suitable for the formation of acid addition salts of this type. Suitable acids, are, for example, hydrogen chloride, hydrogen bromide, naphthalenedisulphonic acids, in particular 1,5-naphthalenedisulphonic acid, phosphoric, nitric, sulphuric, oxalic, lactic, tartaric, acetic, salicylic, benzoic, formic, propionic, pivalic, diethyl acetic, malonic, succinic, pimelic, fumaric, maleic, malic, sulphamic, phenylpropionic, gluconic, ascorbic, isonicotinic, methanesulphonic, p-toluenesulphonic, citric or adipic acid. The acid addition salts may be prepared as is customary, by combining the components, expediently in a suitable solvent or diluent. The acid addition salts are obtained in the synthesis of the compounds of the formula Ia.

The free compounds of the general formula I can optionally be isolated from the acid addition salts in a known manner, e.g. by dissolving or suspending in water and cautiously adding a base, e.g. sodium hydroxide solution and then isolating.

The N-substituted N-nitroso-amino-acetonitriles of the general formula II required as starting compounds can be prepared by a process in which
a) a compound of the general formula IV

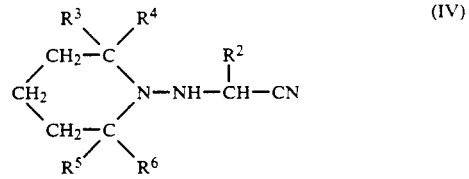

in which $R^2$, $R^3$, $R^4$, $R^5$ and $R^6$ have the meanings already mentioned, is nitrosated, or in which
b) an acid addition salt of a compound of the formula Ia is reacted with a base.

The compounds of the formula IV can be prepared in a manner known per se by the Strecker's aminonitrile synthesis from compounds of the general formula V

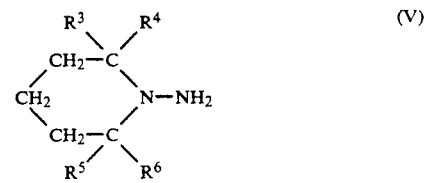

in which $R^3$, $R^4$, $R^5$ and $R^6$ have the meanings already mentioned, by reaction with an aldehyde of the general formula VI $$R^2-\overset{\overset{O}{\|}}{C}-H \quad (VI)$$

in which $R^2$ has the meaning already mentioned, and with hydrocyanic acid or a suitable cyanide, e.g. sodium cyanide or a silyl cyanide, in a suitable solvent, e.g. water.

The nitrosation of the compound of the formula IV is carried out in a known manner, expediently in a suitable inert solvent or solvent mixture, preferably in water, normally at temperatures from 0° to 40° C. and preferably at temperatures from 0° to 10° C. The nitrosation is carried out e.g. with nitrous acid, NO, NOCl or NO-containing gas mixtures. The nitrosation is expediently carried out with nitrous acid, which is advantageously generated from an alkali metal nitrite, e.g. sodium nitrite, and an acid, in particular hydrochloric acid. It is expedient to adjust the aqueous solution of the compound IV to a pH of 1 to 3 with an acid, in particular hydrochloric acid, and to add the alkali metal nitrite dropwise in the form of an aqueous solution to the stirred and cooled solution of the compound.

The solution of the compound II obtained in this case can be directly subjected to the cyclization reaction. However, normally it is appropriate to take up the nitroso compound II first in a suitable organic solvent and to carry out the cyclization to the compounds of the formula Ia in it, optionally after addition of a further solvent.

The compounds of the general formula V are known in some cases or can be prepared, starting from compounds of the general formula VII

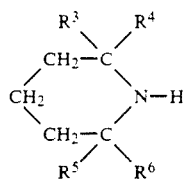

by a process in which either a) a compound of the formula VII is nitrosated to give the N-nitroso compound VIIa and this is then reduced with a suitable reducing agent, for example lithium aluminium hydride:

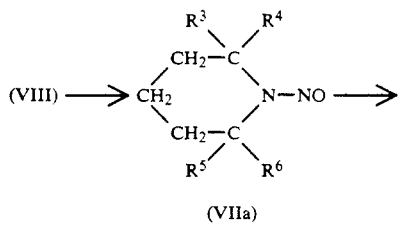

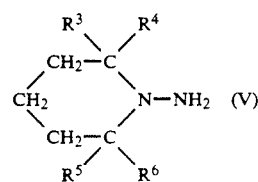

or b) in a manner known per se a compound of the formula VII is converted with potassium cyanate in acid medium into the urea derivative VIII, which is then converted by oxidation with sodium hypochlorite by means of the Hoffmann degradation into the compound V:

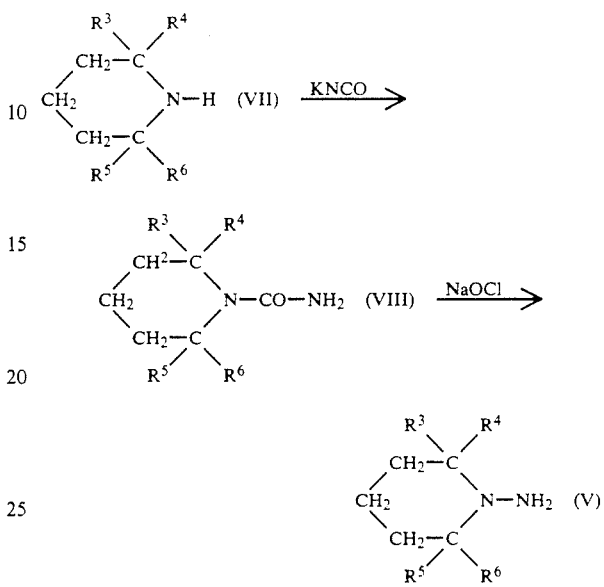

Compounds of the formula II can also be prepared by a process in which an acid addition salt of a compound of the formula Ia, expediently in aqueous solution, is treated with a base, i.e. a compound which gives an alkaline reaction in water, such as e.g. an alkali metal hydroxide, such as e.g. lithium hydroxide, sodium hydroxide or potassium hydroxide, an alkali metal carbonate, such as e.g. lithium carbonate, potassium carbonate or sodium carbonate or an alkali metal bicarbonate, such as e.g. sodium bicarbonate, or an amine, in particular a tertiary amine, such as e.g. triethylamine. The reaction is normally carried out at 10° to 40° C., preferably at room temperature. At least so much base is added that the acid radical is completely bound. As a rule, the acid addition salt is dissolved in water or a mixture of water and solvent and a quantity of base is added such that the aqueous solution gives an alkaline reaction. The binding of the acid radical can also be carried out using an exchanger resin.

The compounds of the formula II can also form acid addition salts with inorganic or organic acids, of which pharmacologically acceptable acid addition salts are preferred. In relation to the formation of these addition salts and suitable acids, the points already stated for the acid addition salts of the compounds I apply.

The compounds of the general formulae I and II and their pharmacologically acceptable acid addition salts have useful pharmacological properties. Their action on the cardiovascular system is particularly pronounced. Compared with known 3-aminosidnone imines, in which the 4-position of the sidnone imine ring only carries a hydrogen atom, the compounds of the general formula I have a prolonged duration of action and/or a greater potency. The same applies to the compounds of the formula II in comparison with other N-nitroso-aminoacetonitriles. The compounds of the formulae I and II and their pharmacologically acceptable acid addition salts lower, for example, the blood pressure as well as the pulmonary artery pressure and the left ventricular end-diastolic pressure and thus contribute to relieving the load on the heart in the sense of an antianginal action, without provoking a reflect tachycardia at the same time.

The compounds of the formulae I and II and their pharmacologically acceptable acid addition salts may therefore be administered to humans as medicaments alone, in mixtures with one another or in the form of pharmaceutical preparations which allow enteral or parenteral use and which contain an effective dose of at least one compound of the formula I and/or II or an acid addition salt thereof as active constituent, in addition to customary pharmaceutically acceptable excipients and additives.

The medicaments may be administered orally, e.g. in the form of pills, tablets, lacquered tablets, coated tablets, hard and soft gelatin capsules, solutions, syrups, emulsions or suspensions or aerosol mixtures. However, administration may also take place rectally, e.g. in the form of suppositories, or parenterally, e.g. in the form of injection solutions, or percutaneously, e.g. in the form of ointments or tinctures.

In order to prepare the pharmaceutical preparations, pharmaceutically inert inorganic or organic excipients may be used. For the preparation of pills, tablets, coated tablets and hard gelatin capsules, e.g. lactose, maize starch or derivatives thereof, talc, stearic acid or salts thereof may be used. Excipients for soft gelatin capsules and suppositories are, e.g. fats, waxes, semisolid and liquid polyols, and natural or hardened oils. Suitable excipients for the preparation of solutions and syrups are e.g. water, sucrose, dextrose, glucose and polyols. Suitable excipients for the preparation of injection solutions are e.g. water, alcohols, glycerol, polyols or vegetable oils.

In addition to the active compounds and excipients, the pharmaceutical preparations may further contain additives such as e.g. fillers, extenders, disintegrants, binders, lubricants, wetting agents, stabilizers, emulsifiers, preservatives, sweeteners, colorants, flavourings or aromatizers, buffer substances, and in addition solvents or solubilizers or agents for achieving a depot effect, and also salts for changing the osmotic pressure, coating agents or antioxidants. They may also contain two or more compounds of the formulae I and/or II their pharmacologically acceptable acid addition salts and other therapeutically active substances.

Other therapeutically active substances of this type are, for example: β-receptor blockers such as e.g. propranolol, pindolol, metoprolol; vasodilators such as, for example, carbochromen; sedatives such as e.g. barbituric acid derivatives, 1,4-benzodiazepines and meprobamate; diuretics such as, for example, chlorothiazide; cardiotonic agents such as e.g. digitalis preparations; hypotensive agents such as e.g. hydralazine, dihydralazine, prazosine, clonidine, Rauwolfia alkaloids; agents which lower the fatty acid level in the blood such as e.g. bezafibrate, fenofibrate; and agents for thrombosis prophylaxis such as e.g. phenprocoumon.

The content of the active compound or the active compounds of the formulae I and/or II in the pharmaceutical preparations can vary within wide limits and is e.g. 0.05 to 50% by weight, preferably 0.05 to 20% by weight. In solid administration forms, such as coated tablets, tablets etc., the content of one or more active compounds of the formulae I and/or II is in many cases 2 to 20% by weight. Liquid administration forms, such as drops, emulsions and injection solutions frequently contain 0.05 to 2% by weight, preferably 0.05 to 1% by weight of one or more active compounds of the formulae I and/or II. The content of one or more active compounds of the formulae I and/or II may partly be replaced in the pharmaceutical preparations, e.g. up to 50% by weight, preferably up to 5 to 40% by weight, by one or more other therapeutically active substances.

The compounds of the formulae I and/or II, their pharmacologically acceptable acid addition salts and pharmaceutical preparations which contain the compounds of the formulae I and/or II or their pharmacologically acceptable acid addition salts as active compounds may be used in humans in the control or prophylaxis of disorders of the cardiovascular system, for example as antihypertensive medicaments in the various forms of high blood pressure, and in the control or prophylaxis of angina pectoris etc. The dosage may vary within wide limits and is to be adjusted to the individual conditions in each individual case. In general, a daily dose of about 0.5 to 500 mg, preferably 1 to 100 mg, per human individual is suitable on oral administration. With other administration forms the daily dose, on account of the good absorption of the active compounds, also lies in similar dose ranges, i.e. in general also at 0.5 to 100 mg/human. The daily dose is normally divided into a number of, for example 2 to 4, part administrations.

The pharmacological action of the compounds of the formula I was determined by a modified method of Godfraind and Kaba (Arch.Int. Pharmacodyn. Ther. 196, (Suppl.) 35 to 49, 1972) and of Schüman et al (Naunyn-Schmiedeberg's Arch. Pharmacol. 289, 409 to 418, 1975). In this connection, spiral strips of the pulmonary artery of the guinea pig are depolarized using 40 mmol/l of potassium after equilibration in calcium-free Tyrode solution. An addition of 0.5 mmol/l of $CaCl_2$ then induces a contraction. The relaxant effect of the test substance is determined by cumulative addition in semilogarithmic graduated concentrations. The concentration of the test substance which inhibits the contraction by 50% (=$IC_{50}$, mol/l) is determined from the concentration-effect curve (abscissa: -log mol/l of test substance, ordinate: % inhibition of the maximum contraction, average value of 4 to 6 vessel strips). The $IC_{50}$ values thus obtained are indicated in the following table. As the comparison with the $IC_{50}$ value of $>3.10^{-4}$ for the known compound molsidomine (N-ethoxycarbonyl-3-morpholino-sydnone imine), compare DE-B1,695,897, shows, the values for the compounds of the formula I are considerably more favourable.

TABLE

| Compound (Example No.) | $IC_{50}$ (mol/l) |
| --- | --- |
| 3 | $2.4 \cdot 10^{-6}$ |
| 6 | $2.3 \cdot 10^{-6}$ |
| 8 | $2.0 \cdot 10^{-6}$ |
| Molsidomine | $>3.0 \cdot 10^{-6}$ |

EXAMPLE 1

3-(2,6-Dimethylpiperidino)-4-methylsydnone imine hydrochloride a) 2-((2,6-Dimethylpiperidino)amino)propionitrile 3.9 9 of sodium cyanide, dissolved in 25 ml of water, and 3.5 g of acetaldehyde, dissolved in 25 ml of methanol, are added dropwise with ice-cooling to a mixture of 7.75 g of 1-amino-2,6-dimethylpiperidine, 50 ml of water and 5.2 ml of concentrated hydrochloric acid. The pH of the solution is adjusted to 7 with hydrochloric acid and the reaction mixture is stirred at room temperature for 2 days. After stripping off the methanol, the mixture is extracted with dichloromethane, and the organic phase is dried with sodium sulphate and concentrated. The residue of 9.2 g of 2-((2,6-dimethylpiperidino)amino)propionitrile which remains is processed further without further purification.

b) 3-(2,6-Dimethylpiperidino)-4-methylsydnone imine hydrochloride

A solution of 3.3 g of sodium nitrite in 20 ml of water is added dropwise with ice-cooling to a mixture of 8.7 g of the intermediate described under a), 50 ml of water and 4.2 ml of concentrated hydrochloric acid. After stirring at 0° C. for 1.5 hours, the pH is adjusted to 5 with sodium carbonate solution, the solution is extracted with ethyl acetate, the organic phase is dried, partly concentrated and 100 ml of a methanolic hydrogen chloride solution are added. Hydrogen chloride is passed into the solution for a further 2 h, the precipitate which deposits after standing in the cold is filtered off with suction, the filtrate is concentrated on a rotary evaporator and the residue is chromatographed on silica gel using dichloromethane/methanol (9:1). 6.7 g of 3-(2,6-dimethylpiperidino)-4-methylsydnone imine hydrochloride are obtained, which after stirring with acetone/diethyl ether and recrystallization from acetone melt at 127° C. with decomposition.

EXAMPLE 2

3-(2,6-Dimethylpiperidino)-N-ethoxycarbonyl-4-methylsydnone imine 0.9 g of sodium hydrogen carbonate is added with ice-cooling to 1.3 g of the 3-(2,6-dimethylpiperidino)-4-methylsydnone imine hydrochloride described under 1) in 20 ml of water and 10 ml of dichloromethane, then a solution of 0.6 g of ethyl chloroformate in 5 ml of dichloromethane is added dropwise and the reaction mixture is stirred at 0° C. for 2 h. The organic phase is separated off, the aqueous phase is extracted with dichloromethane, and the combined organic phases are dried with sodium sulphate and concentrated. The residue is stirred with diethyl ether, undissolved material is filtered off with suction, the filtrate is concentrated on a rotary evaporator, and the residue is triturated with hexane and filtered off with suction.

Yield: 0.95 g of 3-(2,6-dimethylpiperidino)-N-ethoxycarbonyl-4-methylsydnone imine of melting point 62°–65° C.

EXAMPLE 3

3-(2,6-Dimethylpiperidino)-4-hexylsydnone imine hydrochloride a) ((2,6-methylpiperidino)amino)octanonitrile A solution of 9.95 g of sodium cyanide in 50 ml of water and a solution of 23.1 g of heptanal in 20 ml of methanol are added dropwise with ice-cooling to a mixture of 26.0 g of 1-amino-2,6-dimethylpiperidine, 120 ml of water and 17.4 ml of concentrated hydrochloric acid. After adjusting the pH to 7 with hydrochloric acid, the mixture is stirred at room temperature for 2 days. The solution is extracted with dichloromethane, and the combined organic phases are washed with water of pH 4–5 containing hydrochloric acid, dried and concentrated in a rotary evaporator. 42.0 g of 2-((2,6-dimethyl-piperidino)-amino)octanonitrile are obtained, which are employed in the following step without further purification.

b) 3-(2,6-Dimethylpiperidino)-4-hexylsydnone imine hydrochloride

A solution of 11.5 g of sodium nitrite in 30 ml of water is added dropwise with ice-cooling to a mixture of 42.0 g of the aminonitrile intermediate described under a), 100 ml of water and 14.4 ml of concentrated hydrochloric acid. After stirring at 0° C. for 2 hours, the mixture is extracted with ethyl acetate, and the combined organic phases are dried and partly concentrated. After adding 80 ml of methanol, hydrogen chloride is passed in at 0° C. for 1 h. The precipitate which deposits is filtered off with suction, the filtrate is concentrated on a rotary evaporator, the residue is chromatographed on silica gel using dichloromethane/methanol (9:1) and the product is recrystallized from ethyl acetate/acetonitrile.

Yield: 11.8 g of 3-(2,6-dimethylpiperidino)-4-hexylsydnone imine hydrochloride of melting point 144°–145° C. (dec.).

EXAMPLE 4

N-Benzoyl-3-(2,6-dimethylpiperidino)-4-hexylsydnone imine 1.8 g of sodium hydrogen carbonate are added with ice-cooling to 3.6 g of the 3-(2,6-dimethylpiperidino)-4-hexylsydnone imine hydrochloride described under 3) in 40 ml of water and 20 ml of dichloromethane, then a solution of 2.0 g of benzoyl chloride in 10 ml of dichloromethane is added dropwise and the reaction mixture is stirred at 0° C. for 2 h. The organic phase is separated off, the aqueous phase is extracted with dichloromethane, and the combined organic phases are dried and concentrated in a rotary evaporator. The residue is chromatographed on silica gel using dichloromethane and dichloromethane/methanol (98:2). 1.4 g of N-benzoyl-3-(2,6-dimethylpiperidino)-4-hexylsydnone imine are obtained as an oil.

EXAMPLE 5

3-(2,6-Dimethylpiperidino)-4-isopropylsydnone imine hydrochloride a)
2-((2,6-Dimethylpiperidino)amino)-3-methylbutyronitrile A solution of 4.9 g of sodium cyanide in 10 ml of water and a solution of 7.2 g of isobutyraldehyde in 30 ml of methanol are added dropwise with ice-cooling to a mixture of 6.4 g of 1-amino-2,6-dimethylpiperidine, 60 ml of water and 8.6 ml of concentrated hydrochloric acid. After stirring at room temperature for 8 days, the methanol is stripped off on a rotary evaporator and the solution is extracted with dichloromethane. The combined organic phases are washed with water of pH 5 containing acetic acid, dried and concentrated. 11.2 g of 2-((2,6-dimethylpiperidino)amino)-3-methylbutyronitrile remain, which are employed in the following step without further purification.

b) 3-(2,6-Dimethylpiperidino)-4-isopropylsydnone imine hydrochloride

A solution of 4.1 g of sodium nitrite in 20 ml of water is added dropwise with ice-cooling to a mixture of 10.9 g of the intermediate described under a), 50 ml of water and 5.1 ml of concentrated hydrochloric acid. After stirring for 3 hours, the mixture is adjusted to pH 5 with sodium hydrogen carbonate solution and extracted with ethyl acetate. The combined extracts are dried and partly concentrated, and 50 ml of methanol are added. Hydrogen chloride is passed in for 40 min. The precipitate which deposits is filtered off with suction, the filtrate is concentrated on a rotary evaporator and the residue is chromatographed on silica gel using dichloromethane/methanol (9:1). After stirring with acetone, 1.2 g of 3-(2,6-dimethylpiperidino)-4-isopropylsydnone imine hydrochloride are filtered off with suction, which, after recrystallization from acetone/isopropanol/diethyl ether, melt from 110° C. with decomposition.

EXAMPLE 6

4-Benzyl-3-(2,6-dimethylpiperidino)sydnone imine hydrochloride a)

2-((2,6-Dimethylpiperidino)amino)-3-phenylpropionitrile 7.4 g of sodium cyanide, dissolved in 40 ml of water, and 18.0 g of phenyl acetaldehyde, dissolved in 30 ml of methanol, are added dropwise with ice-cooling to a mixture of 12.8 g of 1-amino-2,6-dimethylpiperidine, 60 ml of water and 8.6 ml of concentrated hydrochloric acid. The reaction mixture is stirred at room temperature for 3 days and extracted with dichloromethane. The combined organic phases are washed with water of pH 4-5 containing acetic acid, dried and concentrated in a rotary evaporator. 32.5 g of 2-((2,6-dimethylpiperidino)amino)-3-phenylpropionitrile are obtained, which are reacted further without further purification.

b) 4-Benzyl-3-(2,6-dimethylpiperidino)sydnone imine hydrochloride

A solution of 8.6 g of sodium nitrite in 20 ml of water is added dropwise with ice-cooling to a mixture of 32.0 g of the intermediate described under a), 60 ml of water and 10.6 ml of concentrated hydrochloric acid. After addition of 30 ml of tetrahydrofuran, the mixture is stirred at 0° C. for 2 h and extracted with ethyl acetate. The combined extracts are dried and partly concentrated, and 100 ml of methanolic hydrogen chloride solution are added. Hydrogen chloride is passed in with ice-cooling for 2 h. The precipitate which deposits is filtered off with suction, and the filtrate is concentrated and chromatographed on silica gel using dichloromethane/methanol (9:1). After stirring with isopropanol and diethyl ether, 9.2 g of 4-benzyl-3-(2,6-dimethylpiperidino)sydnone imine hydrochloride are obtained, which melt at 153° C. after recrystallization from acetone.

EXAMPLE 7

4-Benzyl-3-(2,6-dimethylpiperidino)-N-ethoxycarbonylsydnone imine 1.6 g of sodium hydrogen carbonate are added to 3 g of the 4-benzyl-3-(2,6-dimethylpiperidino)sydnone imine hydrochloride described under 6) in 40 ml of water and 20 ml of dichloromethane, then a solution of 1.2 g of ethyl chloroformate in 10 ml of dichloromethane is added dropwise and the reaction mixture is stirred at 0° C. for 2 h. The organic phase is separated off, the aqueous phase is extracted with dichloromethane, and the combined organic phases are dried and concentrated in a rotary evaporator. The residue crystallizes on triturating with diethyl ether.

Yield: 1.4. g of 4-benzyl-3-(2,6-diemthylpiperidino)-N-ethoxy carbonylsydnone imine of melting point 94°-96° C.

EXAMPLE 8

3-(2,6-Dimethylpiperidino)-4-(2-phenylethyl)sydnone imine hydrochloride a)

2-((2,6-Dimethylpiperidino)amino)-4-phenylbutyronitrile

A solution of 5.4 g of sodium cyanide in 20 ml of water and a solution of 14.7 g of 3-phenylpropionaldehyde in 15 ml of methanol are added dropwise with ice-cooling to a mixture of 12.8 g of 1-amino-2,6-dimethylpiperidine, 60 ml of water and 9.4 ml of concentrated hydrochloric acid. The pH is adjusted to 7 with hydrochloric acid and the reaction mixture is stirred at room temperature for 3 days. The mixture is extracted with dichloromethane and the combined extracts are washed with water of pH 4 containing hydrochloric acid, dried and concentrated in a rotary evaporator. 28.9 g of 2-((2,6-dimethylpiperidino)amino)-4-phenylbutyronitrile are obtained, which are employed in the following step without further purification.

b)

3-(2,6-Dimethylpiperidino)-4-(2-phenylethyl)sydnone imine hydrochloride

A solution of 6.9 g of sodium nitrite in 20 ml of water is added dropwise with ice-cooling to a mixture of 28.6 g of the amino butyronitrile described under a), 50 ml of water and 8.6 ml of concentrated hydrochloric acid. After stirring at 0° C. for 2 hours, the mixture is extracted with ethyl acetate, the combined organic phases are dried and partly concentrated, and 100 ml of a methanolic hydrogen chloride solution are added. Hydrogen chloride is passed in with ice-cooling for 1 h, the solution is concentrated on a rotary evaporator, the residue is stirred with diethyl ether and acetonitrile, the precipitate is filtered off with suction, the filtrate is concentrated on a rotary evaporator and the residue is chromatographed on silica gel using dichloromethane/methanol (9:1). After recrystallization from acetonitrile/acetone, 9.6 g of 3-(2,6-dimethylpiperidino)-4-(2phenylethyl)sydnone imine hydrochloride of melting point 158°-160° C. are obtained.

EXAMPLE 9

N-Benzoyl-3-(2,6-dimethylpiperidino)-4-(2-phenylethyl)sydnone imine 1.6 g of sodium hydrogen carbonate are added with ice-cooling to 3.0 g of the 3-(2,6-dimethylpiperidino)-4-(2-phenylethyl)sydnone imine hydrochloride described under 8) in 30 ml of water and 15 ml of dichloromethane, then a solution of 1.4 g of benzoyl chloride in 5 ml of dichloromethane is added dropwise. The mixture is stirred at 0° C. for 2 h, the organic phase is separated off, the aqueous phase is extracted with dichloromethane, the combined organic phases are dried and concentrated in a rotary evaporator. Recrystallization of the residue from hexane yields 2.6 g of N-benzoyl-3-(2,6-dimethylpiperidino)-4-(2-phenylethyl)sydnone imine of melting point 97°-98° C.

Pharmaceutical preparations are described in the following Examples A to F.

Example A
Soft gelatin capsules, containing
5 mg of active compound per capsule:

|  | per capsule |
|---|---|
| Active compound | 5 mg |
| Triglyceride mixture fractionated from coconut oil | 150 mg |
| Capsule contents | 155 mg |

Example B
Injection solution, containing 1
mg of active compound per ml:

|  | per ml |
|---|---|
| Active compound | 1.0 mg |
| Polyethylene glycol 400 | 0.3 ml |
| Sodium chloride | 2.7 mg |
| Water for injection purposes | to 1 ml |

Example C
Emulsion, containing 3 mg of active compound per 5 ml

|  | per 100 ml of emulsion |
|---|---|
| Active compound | 0.06 g |
| Neutral oil | q.s. |
| Sodium carboxymethyl cellulose | 0.6 g |
| Polyoxyethylene stearate | q.s. |
| Glycerol, pure | 0.2 to 2.0 g |
| Flavouring | q.s |
| Water (demineralized or distilled) | to 100 ml |

Example D
Rectal medicament form, containing 4 mg of active compound per suppository

|  | per suppository |
|---|---|
| Active compound | 4 mg |
| Suppository base | to 2 g |

Example E
Tablets, containing 2 mg of active compound per tablet

|  | per tablet |
|---|---|
| Active compound | 2 mg |
| Lactate (finely ground) | 2 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
|  | 311 mg |

Example F
Coated tablets, containing 1 mg of active compound per coated tablet

|  | per coated tablet |
|---|---|
| Active compound | 1 mg |
| Maize starch | 100 mg |
| Lactose | 60 mg |
| sec Calcium phosphate | 30 mg |
| Soluble starch | 3 mg |
| Magnesium stearate | 2 mg |
| Colloidal silica | 4 mg |
|  | 200 mg |

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

I claim:

1. 4-Benzyl-3-(2,6-dimethylpiperidino)sydnone imine and its pharmacologically acceptable acid addition salts.

2. 3-(2,6-Dimethylpiperidino)-4-(2-phenethyl)sydnone imine and its pharmacologically acceptable acid addition salts.

3. 4-Benzyl-3-(2,6-dimethylpiperidino)sydnone imine hydrochloride.

4. 3-(2,6-Dimethylpiperidino)-4-(2-phenethyl)sydnone imine hydrochloride.

5. 3-(2,6-Dimethylpiperidino)-4-hexylsydnone imine and its pharmacologically acceptable acid addition salts.

6. 3-(2,6-Dimethylpiperidino)-4-hexylsydnone imine hydrochloride.

7. N-Benzoyl-3-(2,6-dimethylpiperidino)-4-hexylsydnone imine.

8. 4-Benzyl-3-(2,6-dimethylpiperidino)-N-ethoxycarbonylsydnone imine.

9. N-Benzoyl-3-(2,6-dimethylpiperidino)-4-(2-phenethyl)sydnone imine.

* * * * *